(12) United States Patent
Dearmond et al.

(10) Patent No.: US 11,666,700 B2
(45) Date of Patent: Jun. 6, 2023

(54) SIGNALING UNIT DESIGNED TO INTRODUCE VIBRATIONAL IMPULSE PATTERNS INTO AN INTRAVENOUS FLUID COLUMN

(71) Applicants: Daniel T Dearmond, San Antonio, TX (US); John H. Calhoon, San Antonio, TX (US)

(72) Inventors: Daniel T Dearmond, San Antonio, TX (US); John H. Calhoon, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 232 days.

(21) Appl. No.: 15/753,518

(22) PCT Filed: Aug. 19, 2016

(86) PCT No.: PCT/US2016/047690
§ 371 (c)(1),
(2) Date: Sep. 17, 2018

(87) PCT Pub. No.: WO2017/031394
PCT Pub. Date: Feb. 23, 2017

(65) Prior Publication Data
US 2018/0236165 A1    Aug. 23, 2018

Related U.S. Application Data

(60) Provisional application No. 62/207,230, filed on Aug. 19, 2015.

(51) Int. Cl.
*A61M 5/168* (2006.01)
*A61M 5/00* (2006.01)

(52) U.S. Cl.
CPC ........ *A61M 5/16831* (2013.01); *A61M 5/168* (2013.01); *A61M 5/16854* (2013.01); *A61M 5/16859* (2013.01); *A61M 5/007* (2013.01); *A61M 2005/16863* (2013.01); *A61M 2205/18* (2013.01); *A61M 2205/3334* (2013.01); *A61M 2205/3375* (2013.01)

(58) Field of Classification Search
CPC .............. A61M 5/168; A61M 5/16831; A61M 5/16854; A61M 5/16859; A61M 2005/16863; A61M 2205/3334; A61M 2205/3375; A61M 2005/16868; A61M 2005/16872

See application file for complete search history.

(56) References Cited

U.S. PATENT DOCUMENTS

| 4,764,166 A | 8/1988 | Spani |
| 5,349,852 A | 9/1994 | Kamen et al. |

(Continued)

FOREIGN PATENT DOCUMENTS

| EP | 0361793 | 9/1989 |
| WO | WO 2014/099602 | 12/2013 |

OTHER PUBLICATIONS

International Search Report and Written Opinion issued in Application No. PCT/US2016/047690, dated Oct. 31, 2016.

(Continued)

*Primary Examiner* — James D Ponton

(57) ABSTRACT

Certain embodiments are directed to an inline device(s) for monitoring a fluid path.

9 Claims, 8 Drawing Sheets

(56) References Cited

U.S. PATENT DOCUMENTS

| | | |
|---|---|---|
| 5,768,937 A | 6/1998 | Wajid et al. |
| 6,090,048 A | 7/2000 | Hertz et al. |
| 6,290,681 B1 | 9/2001 | Brown |
| 6,705,319 B1 * | 3/2004 | Wodicka ............ A61M 16/0488 128/207.14 |
| 6,813,964 B1 * | 11/2004 | Clark ................ A61M 5/16813 73/861.52 |
| 2004/0176690 A1 | 9/2004 | Brabrand |
| 2011/0257522 A1 * | 10/2011 | Berard-Andersen ........................ A61M 5/16859 600/438 |
| 2012/0186509 A1 * | 7/2012 | Milijasevic ....... A61M 5/16854 116/266 |
| 2016/0175519 A9 * | 6/2016 | Lee ..................... A61M 5/1452 604/67 |
| 2016/0279366 A1 * | 9/2016 | Mansfield ............. A61M 25/01 |

OTHER PUBLICATIONS

International Preliminary Report on Patentability issued in Application No. PCT/US2016/047690, dated Feb. 20, 2018.
Supplementary European Search Report issued in European Application No. 16837887, dated Feb. 13, 2019.

* cited by examiner

SIGNALING UNIT DESIGNED TO INTRODUCE VIBRATIONAL IMPULSE PATTERNS INTO AN INTRAVENOUS FLUID COLUMN

This application is a national phase application under 35 U.S.C. § 371 of International Application No. PCT/US2016/047690, filed Aug. 19, 2016, which claims priority to U.S. Provisional Patent Application Ser. No. 62/207,230 filed Aug. 19, 2015, each of which is incorporated herein by reference in its entirety.

BACKGROUND

1. Field of the Invention

The invention generally relates to the intravenous delivery of fluids. More particularly, the invention relates to systems and methods of monitoring intravenous catheter/cannula-associated venous occlusion.

2. Description of the Relevant Art

An estimated 250 million intravenous ("IV") devices are placed in hospitals in the United States each year for the delivery of fluids and/or medications. The most common complication of these devices is IV infiltration, also referred to as phlebitis, that may result in substantial patient morbidity and that, at a minimum, requires removal and replacement of the IV. The risk of IV infiltration has been quoted as ranging from 2-67% of all IV lines. In one recent large study, roughly one third of all IV lines had to be replaced due to phlebitis. This has led hospitals to adapt labor-intensive algorithms that involve the regular rotation of IV lines every 2-3 days. Unfortunately, these practices have not clearly been demonstrated to reduce the rates of phlebitis.

Phlebitis leads to venous occlusion, usually the result of a blood clot forming in the vein. When a clot forms in a vein into which (IV) drugs and other fluids are being infused, fluid flow in the vein ceases and fluid flow is diverted to the extra-vascular subcutaneous tissues, (a condition referred to as tissue extravasation or tissue infiltration), causing tissue swelling and tissue damage. Occlusion-related tissue extravasation of drugs and fluids is especially a problem in the elderly owing to the fragile veins in the elderly due to a paucity of supporting tissues. Tissue damage is especially likely when anti-cancer chemotherapy drugs leak into extravascular tissues.

There is, therefore, a need for improved, less labor-intensive phlebitis surveillance.

SUMMARY

Certain embodiments are directed to an inline device for monitoring fluid flow in a cannula or intravenous tube. In certain aspects the inline device comprises a tube through which fluid can be passed coupled to a testing device or signal generator. The fluid can originate from an IV bag or other reservoir and can be caused to flow by a pump, gravity, or other motive force. In certain aspects the testing device or signal generator can include an acoustic wave generator or a pressure wave generator. The acoustic wave or pressure wave generator produces a test signal in the form of an acoustic wave, vibration, or pressure wave that is transferred to fluid contained in or flowing through the device tube. The acoustic wave generator can comprise a compressive, percussive, or vibratory actuator that periodically contacts, strikes, or transfers acoustic waves to the outer surface of the tube in turn generating an acoustic wave pattern within the fluid contained in or flowing through the device. The characteristics or alteration in the characteristics of the propagation of the test signal are indicative of the patency of the cannula or IV. In other aspects the inline device can comprise a compressible portion of tubing or of the intravenous cannula itself that can facilitate the ability of a compressive, percussive, or vibratory actuator to produce a pressure or acoustic wave in the fluid contained in or flowing through the device. In certain aspects the test signal can be generated by manually compressing a portion of the inline device.

The inline device can further comprise a detector for detecting the test signal. The detector can be in communication with a controller that is programed to analyze the test signal.

In certain embodiments, the inline device comprises a dampener, wherein the dampener is composed of a first or second compressible portion of tubing having a compressive strength that is less than the compressive strength of tubing conveying the fluid to and from the inline device. In certain aspects the dimensions of the dampener will change with a change in pressure applied by the fluid in or passing through the device. In a further aspect the pressure applied on the dampener is correlated with the patency of the cannula or IV. A detection device may be coupled to the dampener, wherein the detection device measures changes in the physical dimensions of the dampener during use.

Further embodiments include methods of monitoring delivery or removal of intravenous fluids to or from a subject including coupling an inline device described herein; producing a test signal in the fluid in or flowing through the inline device; monitoring the test signal generated by the inline device; and providing an alert or signal when the test signal indicates an loss or reduction in patency of the cannula or IV. In certain aspects the test signal is reduced or no longer detected in a cannula or IV that is obstructed. The intravenous fluid may be blood, plasma, saline, or other aqueous or non-polar solution. The intravenous fluid may include a medicine or other therapeutic compounds or solutions.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
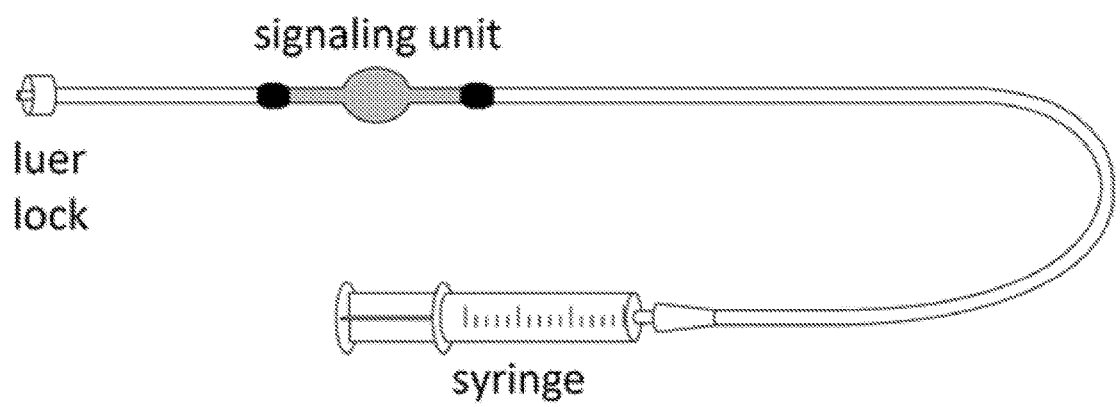
FIG. 1 depicts an embodiment of a signaling unit of a pump system.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

When phlebitis occurs blood vessels become occluded. As a result, fluid flow in the blood vessel ceases and fluid is diverted to the extra-vascular subcutaneous tissues, causing tissue swelling and damage. Conventional IV delivery systems deliver a slow, uniform flow of IV fluids at a set rate which is difficult to monitor and the interruption of such flow may produce a non-specific signal change. The inventors have discovered that a test signal generated in the fluid propagates and is detectable when the fluid pathway is patent. When the fluid path is occluded or closed the test signal is altered, suppressed, or not distinguishable over background.

Certain embodiments are directed to an inline device that can be incorporated into the fluid path. The term "inline" refers to physically locating a component or device between the fluid source and the fluid's intended destination such that the fluid flows through at least a portion of the component or device. The inline device can be configured for placement at any position between the fluid source or reservoir and the entry point into a patient (the fluid's destination). In other embodiments the cannula can be used to remove fluid from a patient in which case the source will be the patient and a fluid collection device the destination. In certain aspects the inline device is integrated into or immediately adjacent to the cannula, needle, or catheter that is to be or is inserted in the patient. In certain aspects the inline device is positioned between the patient and an injection port. In a further aspect multiple inline devices can be placed at different positions along the fluid path, for example one device can be placed adjacent to the patient (proximal relative to the patient), adjacent to the fluid source or reservoir (distal relative to the patient), at various intermediate positions between the fluid source and the patient, proximal to any injection port or valve, and any combinations thereof. In certain aspects the inline device is positioned 1, 2, 3, 4, 5, 6, 7, 8, 9, 10 cm from the tip of the fluid path's destination, and in some instances is integral with the cannula or catheter at the point of insertion. In other aspects the inline device will comprise a connector at both ends that are configured for placing or removing the device from the fluid path.

In certain respects a pump or gravity flow delivers IV fluids/medications to a patient from a fluid source. An inline detector can be included downstream from the fluid source prior to entry into a patient. The inline detector can be configured to produce a detectable test signal in the fluid path of an intravascular delivery system. If the signal is detected the inline detector indicates that the blood vessel is patent; if the signal is absent or is significantly reduced the inline detector indicates that the IV has infiltrated and/or is non-functioning. If irregular or detrimental flow is detected the detector can be configured to produce a signal (e.g. an alarm) alerting a caretaker of to a possible occlusion of the blood vessel.

The devices described herein can be applied in various contexts to decrease the likelihood of occlusion or thrombus formation and/or be able to identify/detect occlusion early, for example, in systems used for delivering nutritional fluids via enteral feeding tubes, in cardiopulmonary bypass circuits or central venous catheters, or for insulin or other drug delivery, etc. The devices can also be employed in arteries, for example during coronary angiography or extremity angiography, with an angiography catheter delivering the signature flow pattern into the artery, where a dampened or absent test signal can signal the presence of critical stenosis of the artery in question.

In certain aspects a device will comprise a microcontroller unit within the device to control test signal generation and detection as well as evaluate data received by the sensors of the device. Various data and information collected or generated by the device can be displayed on a screen that can be associated with the device, pump, fluid source, and/or reservoir; the data can be transmitted to a separate continuous monitoring video screen; the data can be transmitted to a recording or printing device; or any combination thereof.

In another embodiment, a device may be mounted to (e.g., configured to wrap around or integrate into the flow path) an IV tubing between the IV pump and the patient. The device can be configured to act on the IV tubing or the fluid to generate a test signal. In other aspects a device can be configured to act on the fluid flowing through the device for test signal generation and/or monitoring.

A variety of methods or devices may be used to create a test signal. FIG. 1 depicts one embodiment of an inline device. In this example, the IV tubing is modified to contain a signaling unit to generate a test signal. The signaling unit can be a compressible portion configured to produce a test signal when compressed. A sensor can be coupled to the signaling unit. In certain aspect the signaling unit and sensor unit can be positioned at the same or at different positions along the fluid path. In certain aspects a sensor can be placed in a position to monitor the flow in a vein in which the fluid is being introduced, e.g., Doppler sensor. Normal IV tubing is made of polymers that are flexible but relatively stiff, making it difficult to control the amount of compression on the tubing in a reliable manner. The incorporation into the tubing of a segment of softer, more readily compressible material (e.g., silicone) which readily regains its shape allows test signals to be generated in the fluid column within the IV tubing, catheter, and cannulated vein. As shown in FIG. 1, the tubing can be connected to a source (e.g., syringe, IV bag etc.) at one end and a connector (e.g., luer lock) at the other end. The signaling unit can be a soft material such as silicone or a harder material that transmits vibration more readily to the fluid column. This region of tubing can be located close to the connector end of the tubing and can contain a wider mid-section which serves as a small reservoir for IV fluid. Typically the tubing is completely filled with IV fluid with air bubbles being expelled via the connector.

The flexibility of a tubing can be characterized by the compressive strength of the material used to form the tubing. As used herein the term compressive strength is the amount of force needed to deform the material (e.g., tubing, signaling unit, etc.). In the embodiment depicted in FIG. 1, the compressive strength of the softer material used to form the signaling unit is less than the compressive strength of the tubing that is used to convey the fluid to and/or from the signaling unit.

Figure 2A:
FIG. 2A-2C depicts different configurations of compressible tubing used as signaling units in a pump system.
Figure 2B:
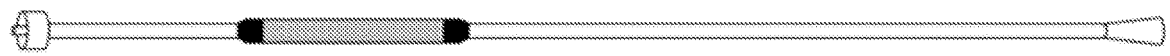
Figure 2C:
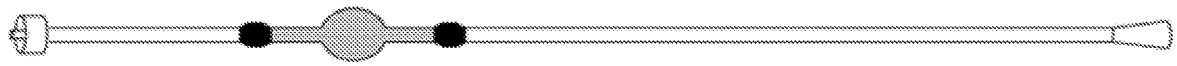

In FIG. 2, different embodiments of the signaling unit are illustrated (signaling units are represented by the gray segments of the IV tubing). In one embodiment (FIG. 2A) the caliber or outer diameter of the signaling unit would be the same as the regular IV tubing. In another embodiment (FIG. 2B) the caliber or diameter of the signaling unit would be larger than the main IV tubing but still substantially cylindrical. In another embodiment (FIG. 2C) the signaling unit would have a diaphragm or reservoir that would be used to deliver test signals into the IV tubing.

Figure 3:
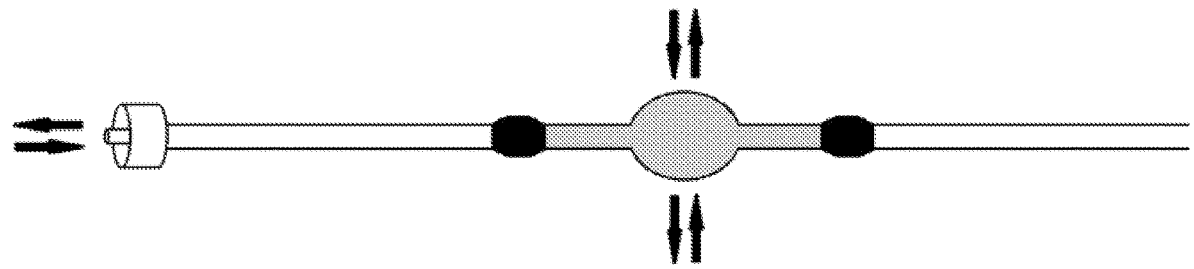
FIG. 3 depicts an illustration of the dynamic function of a signaling unit.

In FIG. 3, an illustration of the dynamic function of an embodiment of a signaling unit is shown. A periodic pattern of compression of the diaphragm/reservoir portion of the signaling unit results in alternate compression and re-expansion of this portion of the IV tubing. This in turn results in compression of the fluid within the IV tubing creating a back and forth or vibrational movement of the fluid at the luer lock end of the tubing. Because the movement of the fluid is back and forth, or vibratory, no net flow of fluid is required for the system to function, i.e., no net fluid administration to the patient is required.

Figure 4:
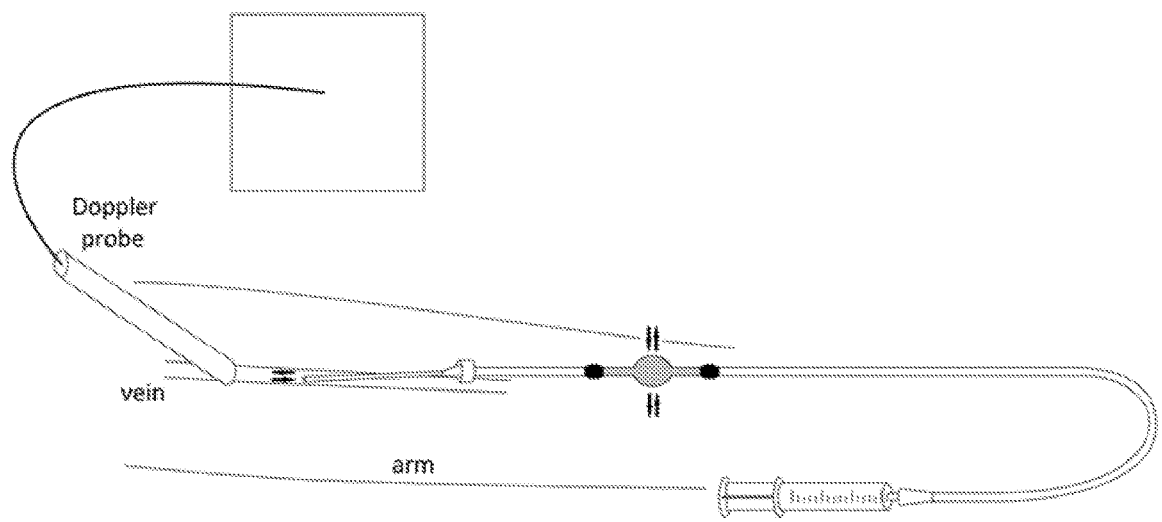
FIG. 4 depicts system coupled with a Doppler probe positioned for monitoring of venous flow.

FIG. 4 shows the IV device connected to an IV catheter which has been placed in a vein. When the signaling unit is compressed, back and forth or vibrational movement of the fluid column is transmitted into the vein of the patient. This back and forth or vibrational movement is detectable by a Doppler probe monitor venous flow in the target vein. Detection of a signal by the Doppler probe confirms that the IV catheter has been successfully placed in the vein and that it is patent and working appropriately. If no signal is detected it can be concluded that there is an interruption in the fluid column somewhere between the signaling unit and the Doppler probe, suggesting either misplacement of the IV catheter or migration out of the vein, which could lead to IV infiltration if not recognized.

Figure 5:
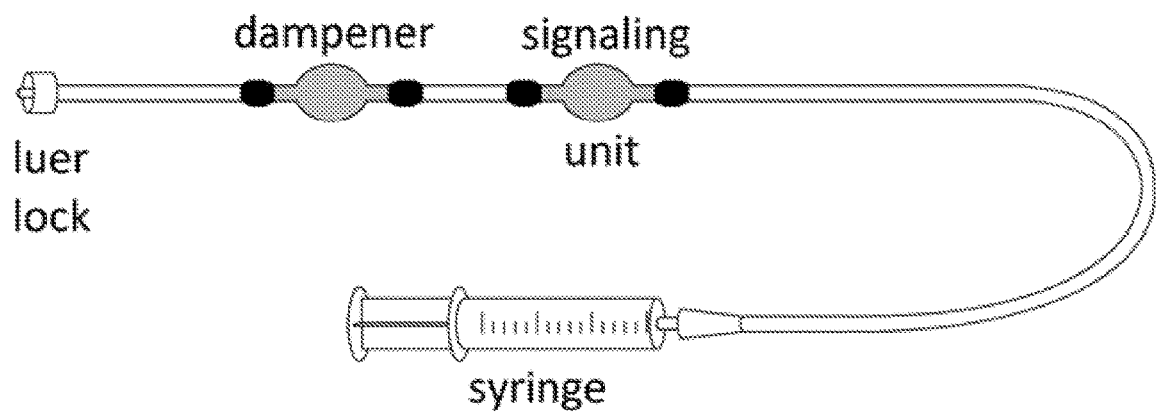
FIG. 5 depicts a pump system that includes a dampening unit and a signaling unit.
Figure 6:
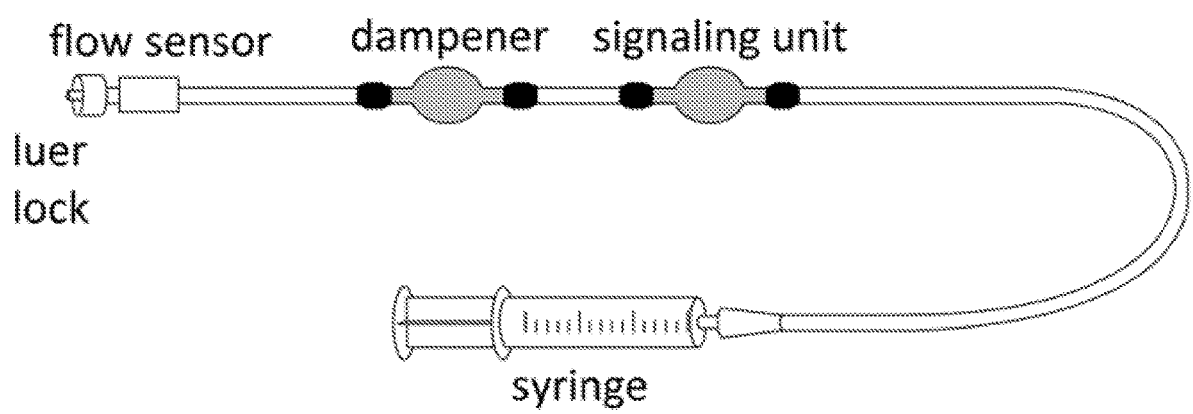
FIG. 6 depicts a system for monitoring venous fluid flow in a subject that includes a dampening unit and a signaling unit

In another embodiment, the tubing system incorporates a dampening unit in addition to the signaling unit (FIG. 5). The dampening unit, similar to the signaling unit, is composed of a segment of softer, more readily compressible material such as silicone which readily regains its shape. The dampener may be incorporated anywhere along the length of the tubing on either side of the signaling unit. The dampener can be used to assist in detection of changes in a test signal. In addition to or in place of the dampening unit, the tubing system may incorporate an acoustic or pressure sensor anywhere along the length of the tubing on either side of the signaling unit (FIG. 6).

Figure 7A:
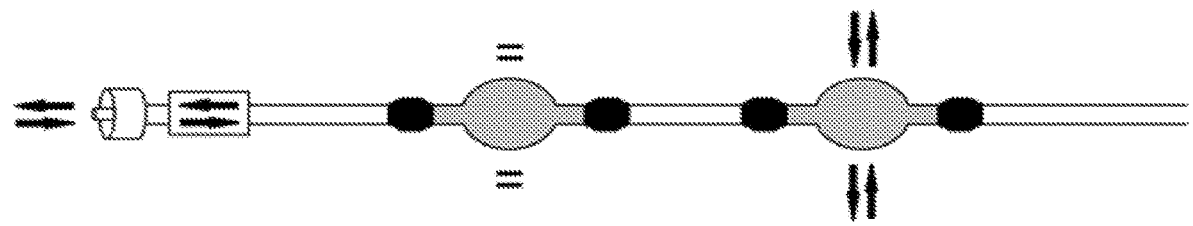
FIG. 7A-7B shows the functionality of the dampener/flow sensor incorporated tubing system for detecting IV occlusion.
Figure 7B:
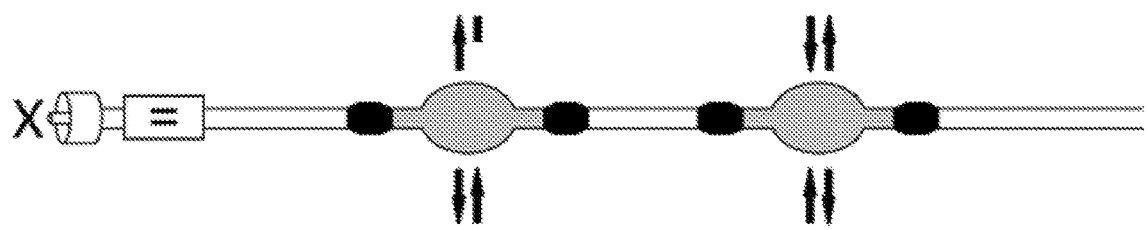

FIG. 7 illustrates one function of the dampener/flow sensor incorporated tubing system for detecting IV occlusion. FIG. 7A, depicts production of a periodic pattern by application of a pattern of compressive force applied to the signaling unit resulting in a back and forth flow out and in to the vein of the patient; this back and forth flow is recorded by a sensor, while no significant changes are detected in the dampener because the force of the fluid compression is being directed longitudinally out of the end of the IV tubing. FIG. 7B depicts the situation in which the fluid path is occluded (as represented by the X adjacent to the luer lock); in this case, the force of periodic fluid compression in the signaling unit cannot be directed longitudinally out of the end of the tubing at the luer lock into the vein of the patient and instead is directed radially generating tension in the wall of the dampener causing the dampener to undergo periodic distention; the flow sensor detects no vibrational fluid movement or flow which confirms the occlusion.

Figure 8A:
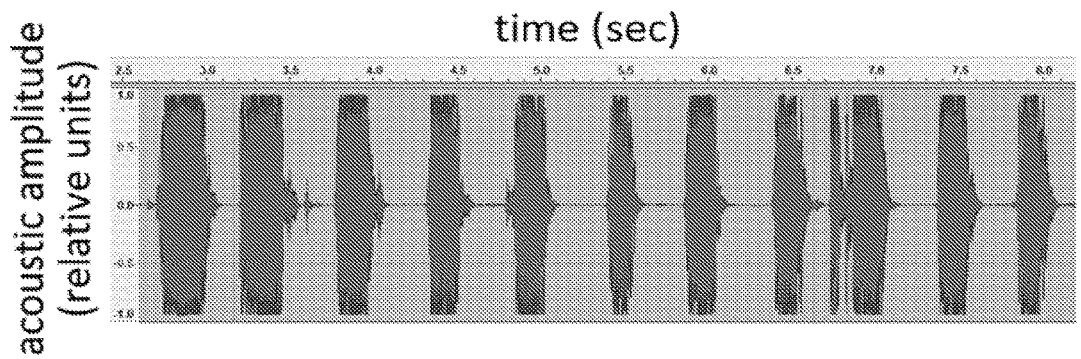
FIG. 8A-8C shows experimental results of an audio signal captured by audio recording software of Doppler signals or pressure changes in the distal IV tubing produced by in a model system.
Figure 8B:
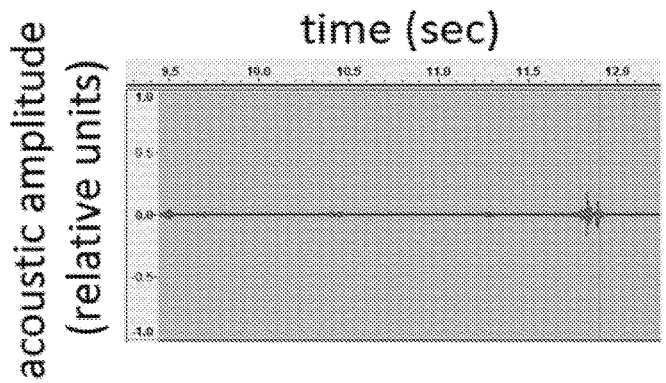
Figure 8C:
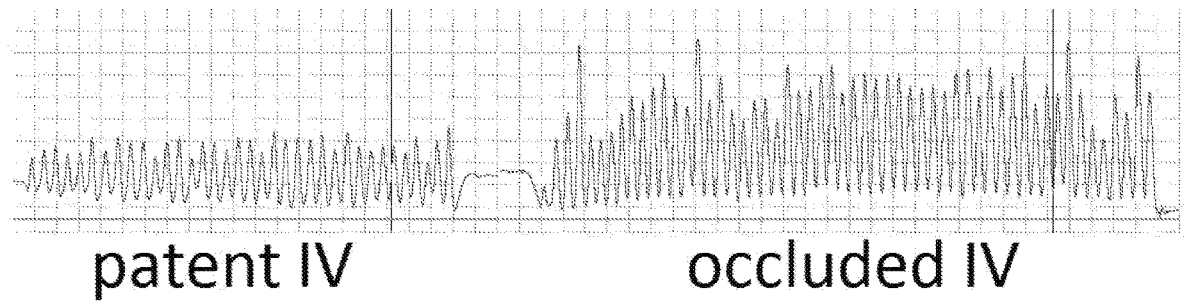

FIG. 8 shows experimental results of an audio signal captured by audio recording software (Audacity) of Doppler signals produced by the experimental set-up in FIG. 7. In FIG. 8A, the signaling unit was manually compressed and allowed to re-expand at a rate of approximately 2 Hz. This produced a readily detectable audio signal pattern that was recorded by the audio recording software and displayed graphically on a computer (FIG. 8A). In FIG. 8B, the IV catheter was occluded at the chosen occlusion site (the distal-most aspect of the IV catheter) and manual compression/release of the signaling unit was again performed at a rate of approximately 2 Hz. With the IV occluded, no flow occurred at the distal end of the signaling unit IV tubing resulting in a lack of audio signal produced by the ultrasound Doppler flow meter (FIG. 8B). This shows that a readily recognizable Doppler audio pattern representing fluid flow can be produced by the signaling unit IV system with incorporated dampener and flow meter, that this audio pattern is detectable in the distal portion of the signaling unit IV system, and that this audio pattern is abrogated by occlusion of the IV catheter, confirming the functionality of the concept submitted for patent protection. In FIG. 8C, instead of a Doppler flow meter, a standard arterial line pressure transducer was used and pressure readings from the distal IV tubing was obtained instead of velocimetric measurements; a distinct pressure difference was observed between a patent and occluded IV.

Figure 9:
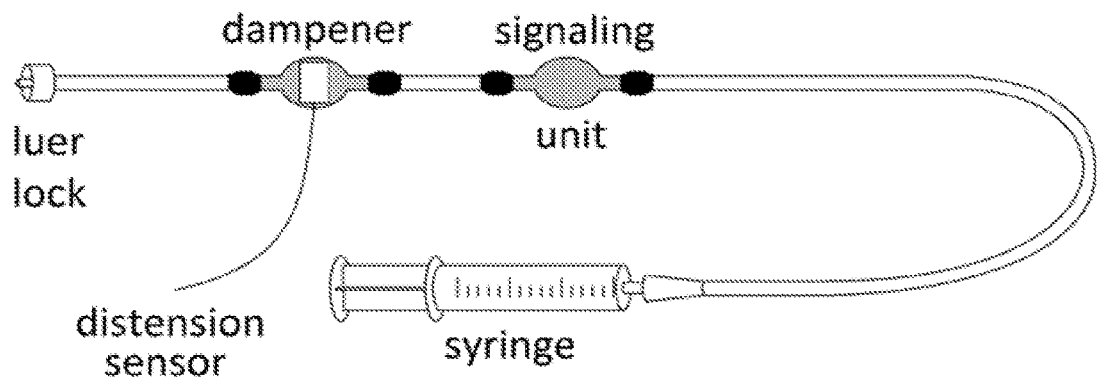
FIG. 9 depicts another embodiment in which the system incorporates a distension sensor coupled to the wall of the dampener to assess IV occlusion.

FIG. 9 depicts another embodiment in which instead of a flow sensor, the system incorporates a distension sensor coupled to the wall of the dampener to assess IV occlusion. The distension sensor may be an ultrasound sensor, bio-impedance sensor, laser sensor, or other type of movement or tension sensor. In the case of IV patency, because the force of fluid compression at the signaling unit is directed out of the end of the IV tubing, no distension occurs in the dampener and the distension sensor records minimal or no changes. If the IV becomes occluded, the force of fluid compression in the signaling unit cannot be directed longitudinally out of the end of the tubing at the luer lock into the vein of the patient and instead is directed radially generating tension in the wall of the dampener causing the dampener to distend. The distension sensor records the change in distension which confirms IV occlusion.

Figure 10:
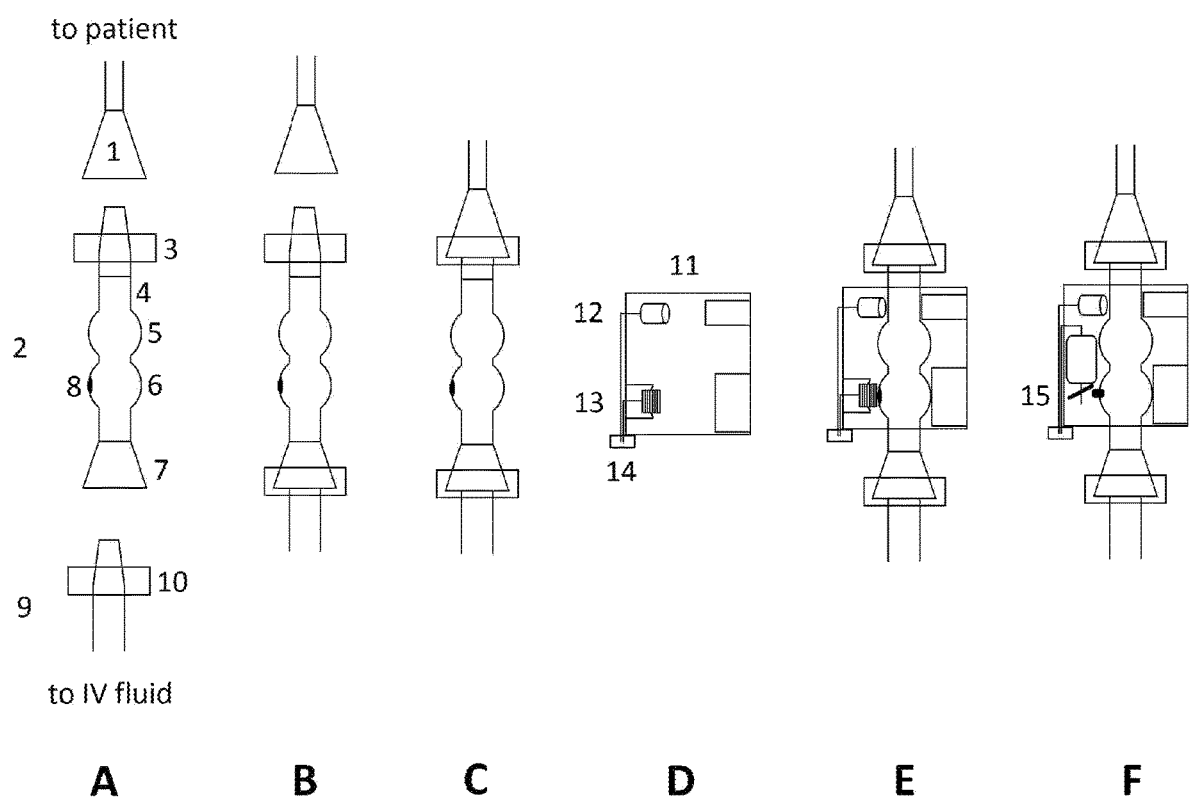
FIG. 10 depict the assembly of the signaling unit IV tubing including a dampener and Doppler window with an embodiment of a housing system.

FIG. 10 depicts, for example, one embodiment of the signaling unit IV tubing with dampener and housing. FIG. 10A depicts an unassembled set of IV components. IV catheter 1 can be positioned in a vein of a patient and coupled to signaling tubing 2 with male luer lock 3 Signaling tubing 2 can have (i) Doppler window 4 to facilitate obtaining Doppler readings from the IV tubing, (ii) dampener 5, signaling unit 6, and female Luer lock 7. In certain aspects signaling unit 2 can have small permanent magnet 8 built into the device. IV tubing 9 can be attached to an IV fluids/medications source and have male Luer lock 10. FIG. 10B depicts an assembled IV system, male luer lock 10 being attached to the IV fluids/medications source and connected via female Luer lock 7 of signaling tubing 2. FIG.

10C depicts the attachment of signaling unit 2 to IV catheter 1 via Luer lock 3. FIG. 10D depicts housing 11 that can contain Doppler flow meter 12 and signal generator 13 (in this case an electromagnet), both of which are connected to an internal power source and wireless transmitter, or in the case of a wired system a connector 14. FIG. 10E depicts the IV catheter/tubing system of FIG. 10 assembled into housing 11. FIG. 10F shows another embodiment of the signal generator in which a motorized rotor 15 strikes an appendage on the signaling unit of the signaling tubing provides mechanical signaling rather than an electromagnetic system. In an embodiment, housing 11 would contain an adhesive located on a patient-contact surface to promote stabilization and retention of the IV catheter.

Figure 11:
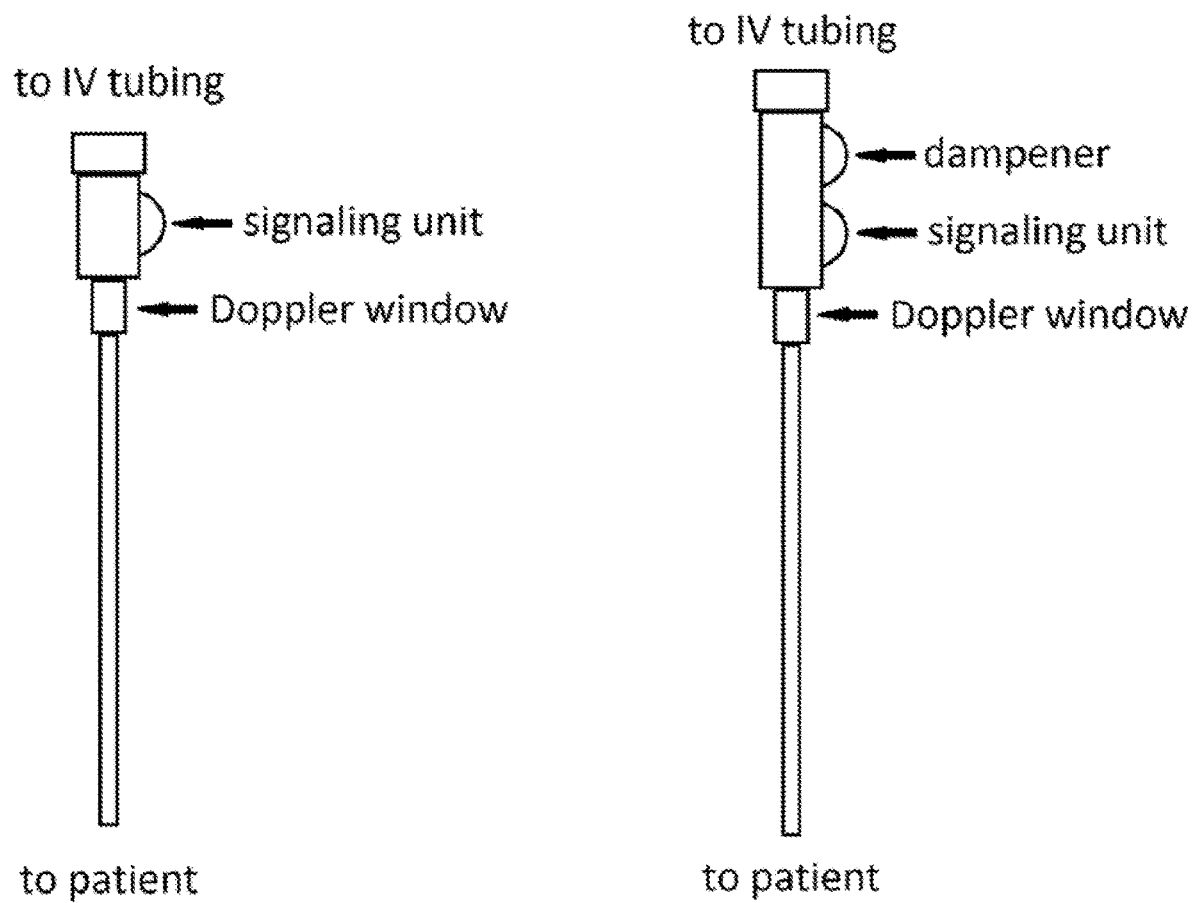
FIG. 11 depicts two embodiments of a signaling unit couplable to an intravenous fluid system.

FIG. 11 depicts an embodiment in which the IV catheter contains the signaling unit, Doppler window, and an optional dampener. In this embodiment, the impulse generating device includes an IV catheter modified to contain a signaling unit. Normal IV catheters are made of polymers that are relatively stiff, making it difficult to control the amount of compression on the IV catheter in a reliable manner. The incorporation into the IV catheter of a segment or portion of softer, more readily compressible material (e.g., silicone) which readily regains its shape allows impulse signals to be transmitted in the fluid column within the IV tubing, catheter, and cannulated vein without requiring any net flow of fluid. As shown in FIG. 11, the IV catheter is connected to IV tubing (and an IV fluid source not shown) at one end and is inserted into the vein of the patient at the other end. The signaling section region of the IV catheter contains a wider mid-section which serves as a small reservoir for IV fluid.

The flexibility of the signaling unit of the IV catheter can be characterized by the compressive strength of the material used to form that portion of the IV catheter. As used herein the term compressive strength is the amount of force needed to deform the shape of the material (e.g., the tubing). In the embodiment depicted in FIG. 11, the compressive strength of the softer material used to form the signaling unit is less than the compressive strength of the IV catheter that is used to convey the fluid to and/or from the signaling unit. In a first embodiment, the IV, in addition to a signaling unit as described above, also contains a Doppler window which represents a material specifically designed to facilitate Doppler measurement at this site. In FIG. 10B, the IV catheter additionally incorporates a dampener.

Figure 12:
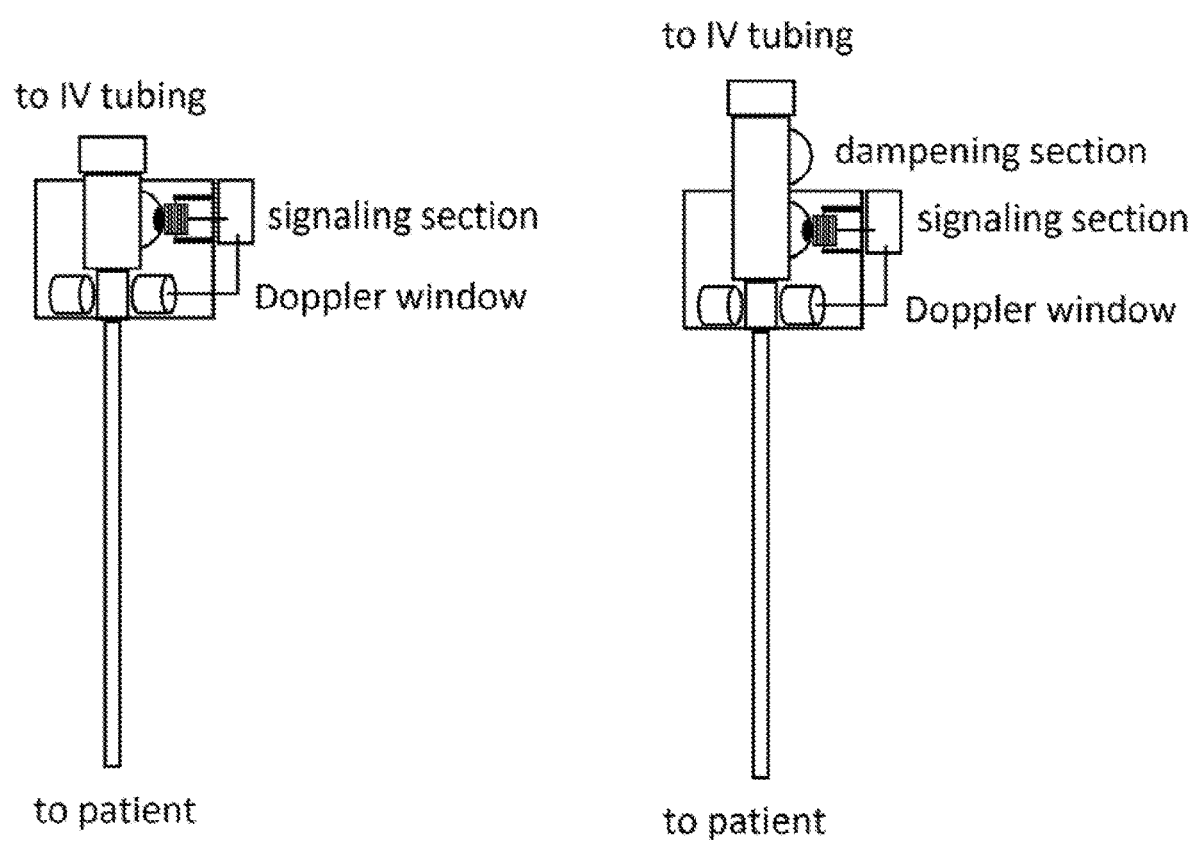
FIG. 12 depicts alternate embodiments of a signaling unit couplable to an intravenous fluid system.

FIG. 12 depicts an embodiment of the signaling unit IV catheter with an optional dampener and housing. In a first embodiment, the signaling unit IV catheter without dampener is assembled into a housing containing a signaling section (here represented by an electromagnet interacting with a permanent magnet on the signaling unit of the IV catheter) and a Doppler window. In in a second embodiment the IV catheter additionally contains a dampener which could be maintained within or just outside of the housing. The Doppler device and signaling section in either case would be powered by a battery contained within the unit or by an external power source. Doppler signals in either case could be transmitted directly by wire or wirelessly to a receiver. In certain aspects, the housing can have an adhesive located on a patient-contact surface to promote stabilization and retention of the IV catheter.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A device for monitoring patency of a fluid path, the device comprising:
a body having a first end configured to couple with a fluid source and a second end configured to couple with an intravenous (IV) or intraarterial (IA) cannula or catheter for delivering fluid to a patient, the body forming a lumen which is part of the fluid path;
a signaling portion configured to generate a test signal by compression of the fluid path generating acoustic waves or pressure waves that propagate longitudinally in the fluid path, wherein the acoustic waves or pressure waves pass through the lumen; and a sensor in contact with the body configured to detect the test signal in the fluid path;
wherein the device is configured (i) to be positioned extra-vascularly and distal to the fluid source when in use, and (ii) to detect intravenous occlusion or intraarterial occlusion.

2. The device of claim 1, further comprising a dampener portion composed of a compressible portion.

3. The device of claim 2, wherein the dampener portion has a compressive strength that is less than a compressive strength of the cannula or the catheter for delivering fluid to a patient.

4. The device of claim 1, further comprising a controller that is in communication with the signaling portion and the sensor.

5. The device of claim 4, wherein the controller is configured to control the signaling portion, receive data from the sensor and analyze the test signal.

6. The device of claim 1, further comprising a housing to encase the body and the signaling portion.

7. The device of claim 1, wherein the test signal is generated by compression, percussion, or an acoustic generator.

8. The device of claim 1, wherein the sensor is an acoustic sensor or a Doppler sensor.

9. A method for monitoring a fluid path comprising:
connecting the device of claim 1 with a target fluid path;
generating a test signal in fluid present in or passing through the device;
monitoring the test signal through one or more sensors of the device of claim 1; and
providing information regarding the patency of the fluid path based on a characteristic of the test signal detected by the one or more sensors.

* * * * *